US012558054B2

(12) United States Patent (10) Patent No.: US 12,558,054 B2
Morita et al. (45) Date of Patent: Feb. 24, 2026

(54) RADIOGRAPHING APPARATUS, RADIOGRAPHING SYSTEM, RADIOGRAPHING METHOD, AND STORAGE MEDIUM

(71) Applicant: CANON KABUSHIKI KAISHA, Tokyo (JP)

(72) Inventors: Hideaki Morita, Tokyo (JP); Toshitaka Noro, Saitama (JP); Asato Kosuge, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 169 days.

(21) Appl. No.: 18/609,509

(22) Filed: Mar. 19, 2024

(65) Prior Publication Data

US 2024/0315658 A1 Sep. 26, 2024

(30) Foreign Application Priority Data

Mar. 22, 2023 (JP) ................................. 2023-045119

(51) Int. Cl.
*A61B 6/00* (2024.01)
(52) U.S. Cl.
CPC .............. *A61B 6/548* (2013.01); *A61B 6/563* (2013.01)

(58) Field of Classification Search
CPC ....... A61B 6/548; A61B 6/563; A61B 6/4233; A61B 6/542; A61B 6/566
See application file for complete search history.

(56) References Cited

U.S. PATENT DOCUMENTS

2017/0227660 A1* 8/2017 Zhang ................... H04W 12/50

FOREIGN PATENT DOCUMENTS

JP 2011120885 A 6/2011

* cited by examiner

*Primary Examiner* — David J Makiya
*Assistant Examiner* — Mamadou Faye
(74) *Attorney, Agent, or Firm* — Canon U.S.A., Inc. IP Division

(57) ABSTRACT

A radiographing apparatus for performing radiographing includes a first communication unit that transmits a radiation image captured in the radiographing via first wireless communication with an access point, a second communication unit that transmits information and receive the information about an establishment of the first wireless communication via second wireless communication with a communication device, and a control unit configured to control the first wireless communication and the second wireless communication. In a case where the radiation image transmission is being performed via the first wireless communication, the control unit performs control to disable at least one of transmission of the information and reception of the information via the second wireless communication.

15 Claims, 10 Drawing Sheets

Figure 1:
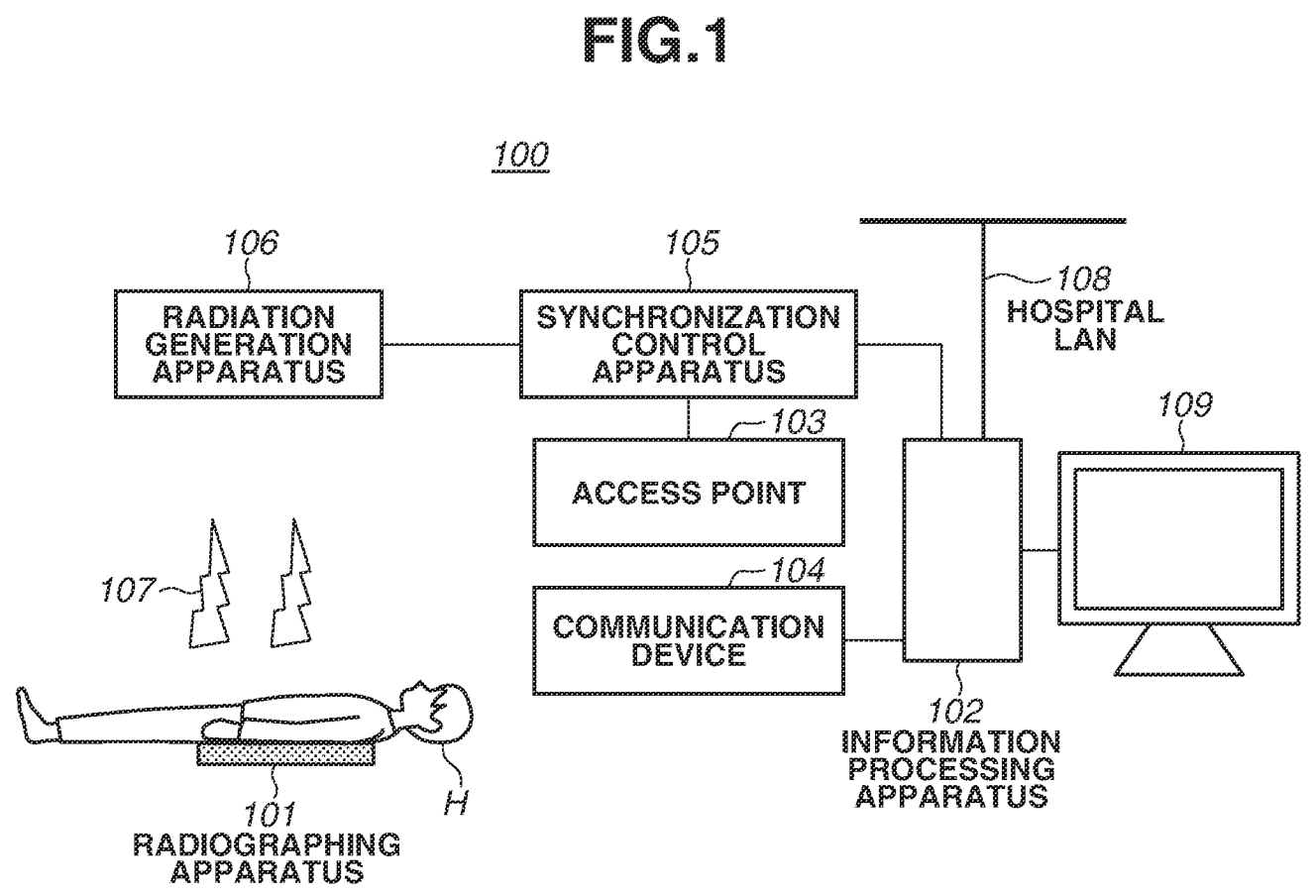

108 HOSPITAL LAN

109

102 INFORMATION PROCESSING APPARATUS

105 SYNCHRONIZATION CONTROL APPARATUS

103 ACCESS POINT

104 COMMUNICATION DEVICE

106 RADIATION GENERATION APPARATUS

107

101 RADIOGRAPHING APPARATUS

H

RADIOGRAPHING APPARATUS, RADIOGRAPHING SYSTEM, RADIOGRAPHING METHOD, AND STORAGE MEDIUM

BACKGROUND

Field

The present disclosure relates to a radiographing apparatus, a radiographing system, a radiographing method, and a storage medium.

Description of the Related Art

With the increase in the use of radiographing apparatuses for generating a digital radiation image based on an emitted radiation in recent years, the digitization of radiographing systems is also advancing. The digitization of radiographing systems has enabled image confirmation immediately after radiographing and remarkably improved the workflow in comparison with a conventional radiographing method using a film or a computed radiography (CR) apparatus.

The development of wireless radiographing apparatuses has facilitated the operation of radiographing apparatuses. Since such wireless radiographing apparatuses are used in a plurality of radiographing systems, there has been proposed a technique for easily linking a radiographing apparatus and a radiographing system.

Japanese Patent Application Laid-Open No. 2011-120885 discusses a technique for linking a radiographing apparatus and an access point by using a short-distance wireless communication unit different from a wireless communication unit used for radiation image transmission and reception.

SUMMARY

According to an aspect of the present disclosure, a radiographing apparatus for performing radiographing includes a first communication unit configured to transmit a radiation image captured in the radiographing, via first wireless communication with an access point, a second communication unit configured to transmit information and receive the information about an establishment of the first wireless communication, via second wireless communication with a communication device, and a control unit configured to control the first wireless communication and the second wireless communication. In a case where the radiation image transmission is being performed via the first wireless communication, the control unit performs control to disable at least one of transmission of the information and reception of the information via the second wireless communication.

Further features of the present disclosure will become apparent from the following description of exemplary embodiments with reference to the attached drawings.

BRIEF DESCRIPTION OF THE DRAWINGS

FIG. 1 illustrates an example of a radiographing system according to a first exemplary embodiment.

DESCRIPTION OF THE EMBODIMENTS

Figure 2:
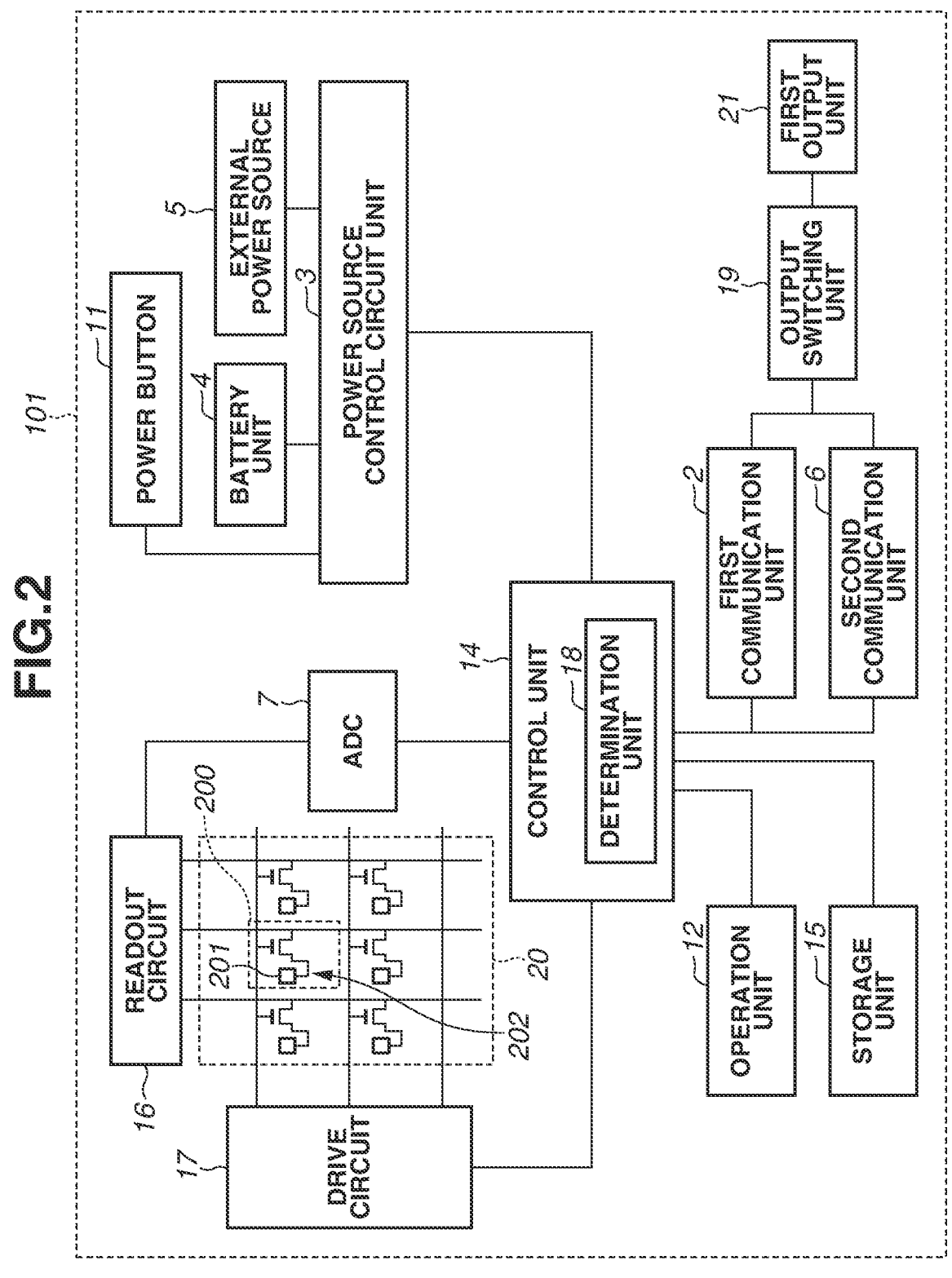
FIG. 2 is an example of an overall configuration of an essential part of a radiographing apparatus according to the first exemplary embodiment.

A first exemplary embodiment will be described below with reference to FIGS. 1 to 7. A configuration of a radiographing system 100 according to the first exemplary embodiment will be described with reference to FIG. 1. The radiographing system 100 includes a radiographing apparatus 101, an information processing apparatus 102, an access point 103, a synchronization control apparatus 105, and a radiation generation apparatus 106.

The radiographing apparatus 101 captures a radiation image based on a radiation 107 that penetrates a subject H. The radiographing apparatus 101 includes, for example, a portable radiographing apparatus.

The information processing apparatus 102 displays a radiation image captured by the radiographing apparatus 101 on a display unit 109 and issues an imaging condition instruction input via an operation unit (not illustrated) to the radiographing apparatus 101. The information processing apparatus 102 transmits setting information for enabling wireless communication between the radiographing apparatus 101 and the information processing apparatus 102.

The access point 103 is a radio wave relaying apparatus for wirelessly exchanging information with the radiographing apparatus 101.

A communication device 104 is a radio wave receiver/transmitter for performing short-distance communication between the radiographing apparatus 101 and the information processing apparatus 102. For example, the communication device 104 is a dongle that is connected to the information processing apparatus 102 via a universal serial bus (USB) interface. A function incorporated in other apparatuses, such as the radiation generation apparatus 106, can also be used instead of the communication device 104.

The communication device 104 conforms to at least the Bluetooth® Basic Rate/Enhanced Data Rate (BR/EDR) or Bluetooth® Low Energy (LE) standards.

The communication device 104 has a function of a radio frequency identifier (RFID) device that exchanges information through short-distance wireless communication using an electromagnetic field or radio wave from a tag with embedded identification (ID) information. Applicable RFID communication methods include an electromagnetic induction method or a radio wave method. The communication device 104 can also have the function of an access point.

The synchronization control apparatus 105 includes a circuit for intermediating communication and monitors the statuses of the radiographing apparatus 101 and the radiation generation apparatus 106. For example, the synchronization control apparatus 105 controls the emission of the radiation 107 from the radiation generation apparatus 106 and the radiographing of the subject H by the radiographing apparatus 101. The synchronization control apparatus 105 can include a hub for connecting a plurality of network apparatuses.

To produce the radiation 107, such as an X-ray, the radiation generation apparatus 106 includes a radiation tube that accelerates electrons with a high voltage to make the electrons collide with the anode. The radiation 107 can be an alpha ray, a beta ray, a gamma ray, an X-ray, or neutron radiation.

A hospital local area network (LAN) 108 is a local area network located in a hospital. In the radiographing system 100 illustrated in FIG. 1, the subject H is a patient irradiated with the radiation 107 emitted from the radiation generation apparatus 106. The radiographing apparatus 101 detects the radiation 107 that penetrates the subject H and generates a radiation image.

In the above-described state, the radiographing system 100 can perform the radiographing through synchronous imaging and asynchronous imaging.

In synchronous imaging, the radiographing apparatus 101 and the radiation generation apparatus 106 exchange electrical synchronization signals to synchronize the imaging timing with the radiation emission.

In asynchronous imaging, in contrast, the radiographing apparatus 101 and the radiation generation apparatus 106 do not exchange electrical synchronization signals. Instead, the radiographing apparatus 101 starts the radiographing upon detection of the radiation incidence. In asynchronous imaging, when the radiation 107 is emitted from the radiation generation apparatus 106 without providing the synchronization control apparatus 105, the radiographing apparatus 101 detects the radiation emission, accumulates image signals (electric charges), and generates a radiation image. In asynchronous imaging, the radiographing apparatus 101 can transfer a radiation image for each radiographing or store a captured image in the radiographing apparatus 101 without transferring the captured image for each radiographing.

The radiographing system 100 can perform the radiographing based on general imaging conditions for the radiographing, such as fluorography, continuous imaging, still image capturing, digital subtraction angiography (DSA), road-map imaging, programmed imaging, tomography, or tomosynthesis imaging.

The imaging conditions include imaging related information, such as the imaging frame rate, tube voltage, tube current, sensor read area, sensor drive binning setting, and collimator diaphragm setting. Other imaging related conditions include auto dose control, auto exposure control (AEC), radiation window width, and whether captured images are accumulated in the radiographing apparatus 101.

In fluorography, for example, the radiation generation apparatus 106 produces a pulsating radiation and performs the radiographing while performing synchronous imaging. In this case, the radiographing system 100 performs the radiographing by setting a sensor read area and sensor drive binning as required.

FIG. 2 illustrates an example of an overall configuration of an essential part of the radiographing apparatus 101 according to the present exemplary embodiment.

A power button 11 is operated by the user to start or stop the power supply to each component of the radiographing apparatus 101. The power button 11 can be provided as a mechanical switch or on a touch panel. While the power button 11 is disposed, for example, on a side face of the radiographing apparatus 101, it can be disposed at any position on the radiographing apparatus 101 on a surface other than the surface in the radiation incident direction.

A battery unit 4 supplies a predetermined voltage to each component of the radiographing apparatus 101. For example, the battery unit 4 is used to supply power to a control unit 14 (described below). The battery unit 4 is formed of, for example, a lithium-ion battery and an electrical double layer capacitor or can be implemented by other known techniques. If power is constantly supplied to the radiographing apparatus 101 from an external power source, the battery unit 4 may not be disposed in the radiographing apparatus 101.

An external power source 5 supplies a predetermined voltage from external to the radiographing apparatus 101. Although a wired power supply method is commonly used, a non-contact power supply is also applicable.

A power source control circuit unit 3 monitors the connection status with the battery unit 4 and the external power source 5, controls the power supply to each component of the radiographing apparatus 101, and monitors the remaining capacity of the battery based on the operating status of the power button 11. For example, the power source control circuit unit 3 transforms the voltage from the battery unit 4 to a predetermined voltage and supplies the transformed voltage to each component of the radiographing apparatus 101. If the external power source 5 is not connected to the radiographing apparatus 101, for example, the power source control circuit unit 3 turns the power supply from the battery unit 4 on or off to each component of the radiographing apparatus 101 upon operation of the power button 11.

A radiation detection unit 20 detects the radiation 107 that penetrates the subject H as image signals (electric charges). For example, the radiation detection unit 20 includes a photoelectric conversion element and a fluorescent substance. The photoelectric conversion element converts light converted by the fluorescent substance into image signals (electric charges) as electrical signals and accumulates the image signals.

A drive circuit 17 is an integrated circuit (IC) that applies a drive signal to the radiation detection unit 20 to instruct the radiation detection unit 20 to perform operations for accumulating and reading out image signals (electric charges). More specifically, when the drive circuit 17 selects pixels 200 in a certain row via the drive signal, switching elements 202 of the pixels 200 in the relevant row are sequentially turned ON. Then, image signals (electric charges) accumulated in photoelectric conversion elements 201 of the pixels 200 in the relevant row are output to signal lines connected with these pixels 200.

A readout circuit 16 having a function of amplifying the image signals (electric charges) output to the signal line sequentially reads out the image signals of the radiation detection unit 20. An analog-to-digital converter (ADC) 7 converts the analog image signals read out by the readout circuit 16 into digital image signals and outputs the image signals to the control unit 14 as a radiation image. More specifically, the ADC 7 configures an analog-to-digital (A/D) conversion unit for converting the analog image signal read out by the readout circuit 16 into digital data.

A storage unit 15 stores radiation image data output from the ADC 7, a system identifier of the radiographing system 100 to be linked, a calculation distance threshold value calculated based on the radio wave intensity between the radiographing apparatus 101 and the communication device 104, and offset images. The storage unit 15 can store the generated image data in association with a transfer history of radiation image data and imaging conditions including radiographer ID as identification information for the attending radiographer, patient ID as identification information for the patient, imaging time, imaging dosage, imaging portion, and the number of captured images.

While a nonvolatile memory such as a flash memory is preferably used for the storage unit 15, the present exemplary embodiment is not limited thereto. A volatile memory, such as a synchronous dynamic random access memory (SDRAM), is also applicable. The storage unit 15 can also be detachable to be attached to and detached from the information processing apparatus 102.

A wireless communication module is set as a first communication unit 2 based on the media used in communication by the information processing apparatus 102 and the synchronization control apparatus 105. For example, the first communication unit 2 can communicate with the access point 103 via a wireless local area network (LAN) and transmit and receive radiation images to and from the information processing apparatus 102. The first communication unit 2 is an example of a communication unit that transmits a radiation image captured in radiographing via first wireless communication with an access point included in the radiographing system 100. The first wireless communication is, for example, wireless communication using the first communication unit 2.

A wireless communication module is set as a second communication unit 6 based on the media used in communication by the information processing apparatus 102 and the synchronization control apparatus 105. For example, the second communication unit 6 communicates with the communication device 104 via a wireless personal area network (PAN). The second communication unit 6 can transmit and receive the identifier of the radiographing system 100, a service set identifier (SSID) and an encryption key to establish the communication with the first communication unit 2 and Internet protocol (IP) address. The second communication unit 6 is an example of a second communication unit that transmits and receive information about the establishment of the first wireless communication via second wireless communication with the communication device 104 included in the radiographing system 100. The second wireless communication is, for example, wireless communication using the second communication unit 6. The information about the establishment is, for example, information to be transmitted and received in packet units. This information can be any type of information as long as it can transmit the address of the access point 103 connected with the information processing apparatus 102 on a one-to-one basis to the radiographing apparatus 101.

The second communication unit 6 can also transmit information about the position and orientation of the radiographing apparatus 101 to the information processing apparatus 102 and the radiation generation apparatus 106. The position and orientation can be acquired by using known techniques of an acceleration sensor, gyro sensor, magnetic field sensor, global positioning system (GPS) sensor, etc. The second communication unit 6 can also set an ID for associating the radiation image with information to be applied to the patient as a subject to the radiographing apparatus 101.

For example, the communication device 104 can transmit patient information input to the information processing apparatus 102 and patient information acquired by a bar code reader having a communication device that can communicate with the second communication unit 6 to the second communication unit 6.

The second communication unit 6 can also transmit the imaging enabled/disabled state of the radiographing apparatus 101 and the status of the battery unit 4 to an external apparatus, such as the information processing apparatus 102 and the radiation generation apparatus 106.

The imaging enabled/disabled state indicates whether power of the radiation detection unit 20, the readout circuit 16, and the drive circuit 17 is turned ON, preparation operations such as a read operation are completed, and the analog image signal read out by the readout circuit 16 can be converted into a digital image signal. The status of the battery unit 4 indicates the charge status of the battery unit 4 including whether power is supplied to the radiographing apparatus 101, the remaining charge capacity of the battery unit 4, and whether the remaining charge capacity of the battery unit 4 is less than or equal to a predetermined value.

An output switching unit 19 changes transmission and reception data of the first communication unit 2 or the second communication unit 6. The output switching unit 19 includes, for example, a switching IC such as an analog switching IC to enable communicating the transmission and reception data of the first communication unit 2 and the second communication unit 6 on a time-sharing basis.

A first output unit 21 converts communication data to be transmitted by the output switching unit 19 into a radio wave and transmits the data.

The first output unit 21 converts the radio wave to be transmitted by the access point 103 and the communication device 104 into communication data. The first output unit 21 includes, for example, a wireless antenna such as a planar antenna and dipole antenna (not illustrated).

An operation unit 12 is a button used as a manual trigger for exchanging the setting information between the radiographing apparatus 101 and the communication device 104. The operation unit 12 can be provided as a mechanical switch or on a touch panel. When the operation unit 12 is operated, the operation unit 12 can transmit and receive the identifier of the radiographing system 100, the SSID and encryption key set in the first communication unit 2. While the operation unit 12 is disposed on a side face of the radiographing apparatus 101, it can be disposed at any position on a surface other than the surface in the radiation incident direction. The operation unit 12 is an example of an operation unit related to the second wireless communication.

The control unit 14 controls each component of the radiographing apparatus 101. There is a demand that the control unit 14 be compact, lightweight, and power-efficient because of the characteristics of the radiographing apparatus 101. To achieve such a demand, a field programmable gate array (FPGA) or a dedicated IC circuit may be used as the control unit 14.

The control unit 14 includes a determination unit 18. When the radiographing apparatus 101 performs the wireless communication via the second communication unit 6, the determination unit 18 determines the status of the radiation image communication via the first communication unit 2. For example, when the radiographing apparatus 101 performs the wireless communication via the second communication unit 6 and the wireless communication via the first communication unit 2 at the same time, a radio wave interference may occur. The present exemplary embodiment therefore changes the communication configuration of at least one of the wireless communication via the first communication unit 2 and the wireless communication via the second communication unit 6 according to the status of the wireless communication via the first communication unit 2.

The radiation image communication status indicates a state in which a radiation image is being communicated or a state where a radiation image can be communicated. For example, the determination unit 18 determines whether a radiation image is being communicated, based on whether a radiation image transmission buffer is present or whether a radiation image communication protocol (e.g., transmission control protocol/Internet protocol (TCP/IP)) is in a connected state. The determination unit 18 determines whether a radiation image can be communicated, based on whether the radiation detection unit 20 completes imaging preparation operations or whether the radiographing apparatus 101 has received an instruction for entering the imaging enabled state from the information processing apparatus 102 and become ready for the radiographing in synchronization with the radiation generation apparatus 106. The completion of the imaging preparation operations of the radiation detection unit 20 is an example of completion of the imaging preparation operations related to radiographing. For example, when the radiation detection unit 20 receives an instruction from the information processing apparatus 102, the radiographing apparatus 101 completes the imaging preparation operations by entering a state of being ready for performing an accumulation operation (imaging enabled state).

The control unit 14 changes the communication configuration of the first communication unit 2 or the communication configuration of the second communication unit 6 based on the result of the determination by the determination unit 18. For example, when the second communication unit 6 communicates the identifier of the radiographing system 100 and the determination unit 18 determines that radiation image information communication via the first communication unit 2 is being performed, the control unit 14 stops the communication via the second communication unit 6. In this case, the control unit 14 may stop the communication by stopping the power supply to the second communication unit 6 or discarding a communication packet or connection. If the imaging preparation operations for the radiographing have been completed, the determination unit 18 as an example of a control unit may perform control to disable at least one of the transmission and reception of information (information about the establishment of the first wireless communication) via the second wireless communication. When the radiation image transmission via the first wireless communication is being performed, the determination unit 18 as an example of a control unit may perform control to disable at least one of the transmission and reception of information (information about the establishment of the first wireless communication) via the second wireless communication.

As an example of a modification of the communication configuration of the control unit 14, the control unit 14 may change the radio wave frequency currently used by the communication unit 2 to a frequency currently unused by the second communication unit 6. For example, if the first communication unit 2 as a wide local area network (WLAN) transmits a radiation image by using the 2.4-GHz band radio wave, and the second communication unit 6 as Bluetooth® performs the communication by using the 2.4-GHz band radio wave, the control unit 14 changes the radio wave frequency of the WLAN to the 5-GHz band.

Alternatively, the control unit 14 may give priority to the communication via the first communication unit 2 over the communication via the second communication unit 6, as another example of a modification of the communication configuration of the control unit 14. For example, when storing a communication packet of the second communication unit 6 and a radiation image communication packet to be transmitted by the first communication unit 2 in the transmission buffer, the control unit 14 may control the communication packet to be transmitted by the first communication unit 2 earlier than the communication packet of the second communication unit 6.

Figure 3:
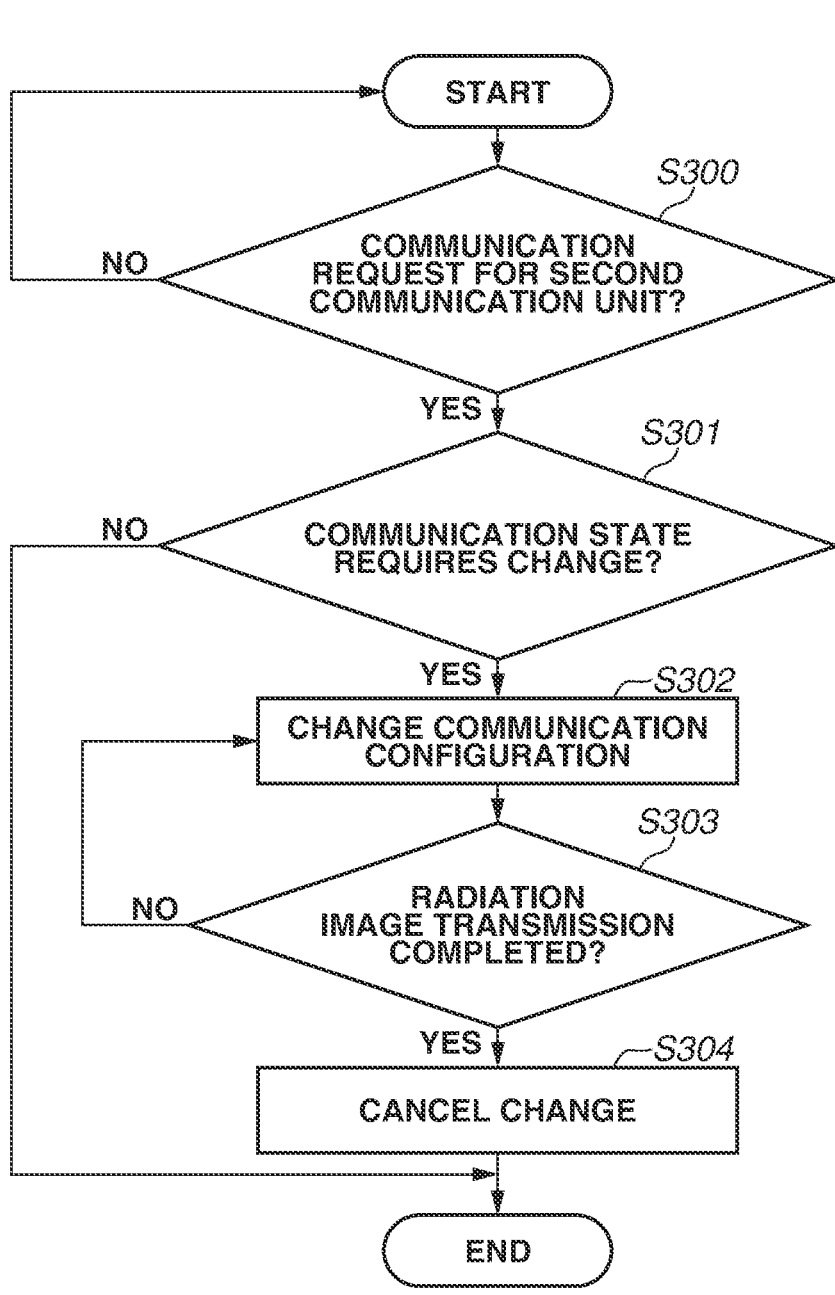
FIG. 3 is a flowchart illustrating operations of the radiographing apparatus according to the first exemplary embodiment.

FIG. 3 is a flowchart illustrating a method for controlling the radiographing apparatus 101 according to the present exemplary embodiment.

In step S300, the determination unit 18 determines whether to perform the wireless communication via the second communication unit 6 depending on the status of a transmission/reception communication buffer and the status of a communication controller. If the control unit 14 is preset to perform the communication via the second communication unit 6 upon operation on the operation unit 12, the determination unit 18 can also determine whether the operation on the operation unit 12 has been performed. If the determination unit 18 determines to perform the wireless communication via the second communication unit 6 (YES in step S300), the processing proceeds to step S301. If the determination unit 18 determines not to perform the wireless communication via the second communication unit 6 (NO in step S300), the determination unit 18 performs the operation in step S300 again.

In step S301, the determination unit 18 determines, when performing the communication via the second communication unit 6, whether the status of the radiation image communication via the first communication unit 2 requires changing the configuration of the communication via the first communication unit 2 or the configuration of the communication via the second communication unit 6. If the determination unit 18 determines that the communication status requires to change the communication configuration (YES in step S301), the processing proceeds to step S302. In contrast, if the determination unit 18 determines that the communication status does not require to change the communication configuration (NO in step S301), the processing ends the flowchart, and the wireless communication via the second communication unit 6 is performed.

In step S302, the control unit 14 changes the communication configuration of the wireless communication via the first communication unit 2 or the second communication unit 6 based on the determination result by the determination unit 18. The processing then proceeds to step S303.

In step S303, the determination unit 18 determines whether the first communication unit 2 has completed the radiation image transmission or the first communication unit 2 has become not ready for the wireless transmission. If the result of the determination is yes (YES in step S303), the processing proceeds to step S304. If the result of the determination is no (NO in step S303), the processing returns to step S302. In other words, the control unit 14 repeats the operations in steps S302 and S303 until the determination unit 18 determines that the state where the first communication unit 2 is performing the wireless communication has ended or the state where the first communication unit 2 is ready for the wireless communication has ended.

In step S304, the control unit 14 cancels the communication configuration change of the wireless communication via the first communication unit 2 or the second communication unit 6 performed in step S302 to restore the communication configuration of the wireless communication before the change in step S302.

Figure 4:
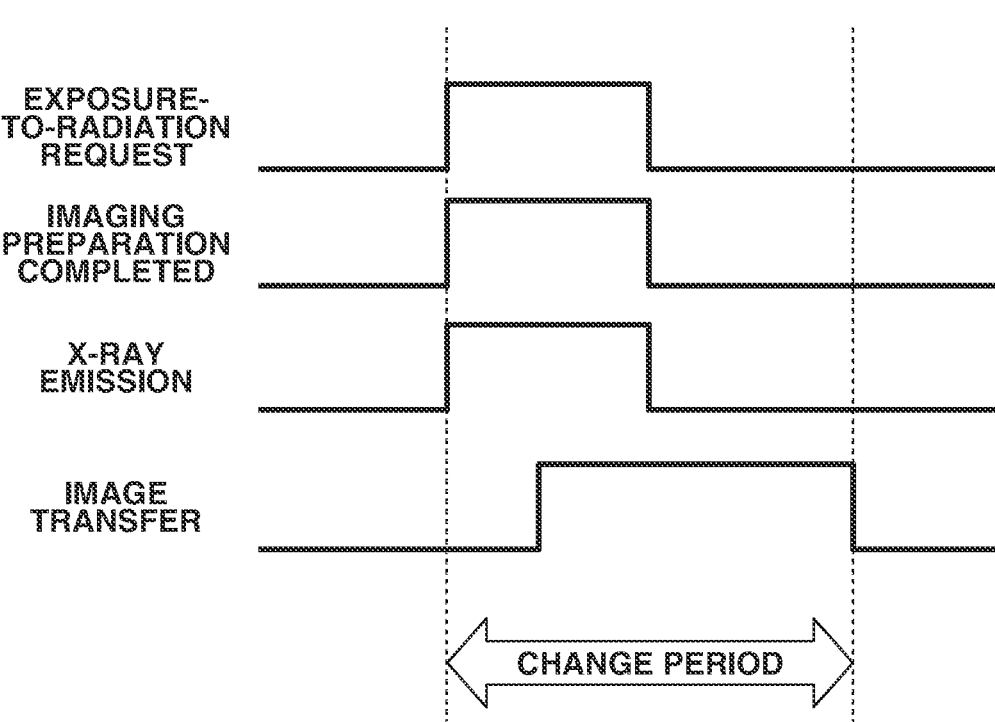
FIG. 4 illustrates a time period during which a control unit according to the first exemplary embodiment changes a communication configuration.

FIG. 4 illustrates an example of a time period during which the control unit 14 changes the communication configuration when the determination unit 18 of the radiographing apparatus 101 according to the present exemplary embodiment determines that it is in a state that the radiation image can be transmitted.

The radiation generation apparatus 106 issues an exposure instruction to the radiographing apparatus 101 via the synchronization control apparatus 105. When the radiographing apparatus 101 receives the imaging preparation instruction from the information processing apparatus 102, and the imaging preparation operations are completed, the radiographing apparatus 101 notifies the radiation generation apparatus 106 that exposure to radiation can be performed, via the synchronization control apparatus 105.

When the radiation generation apparatus 106 receives an exposure-to-radiation enabled notification from the radiographing apparatus 101, the radiation generation apparatus 106 emits a radiation. When the radiographing apparatus 101 issues an exposure-to-radiation enabled notification to the synchronization control apparatus 105, the determination unit 18 determines that the radiation image transmission is enabled. If the determination unit 18 determines to perform the communication via the second communication unit 6, the control unit 14 limits the communication via the first communication unit 2 or the second communication unit 6. More specifically, if the imaging preparation operations for the radiographing have been completed, the determination unit 18 as an example of a control unit performs control to disable at least one of the transmission and reception of information (information about the establishment of the first wireless communication) via the second wireless communication. When the determination unit 18 determines that the radiation image transmission is completed, the control unit 14 performs control to cancel the communication limitation.

Figure 5:
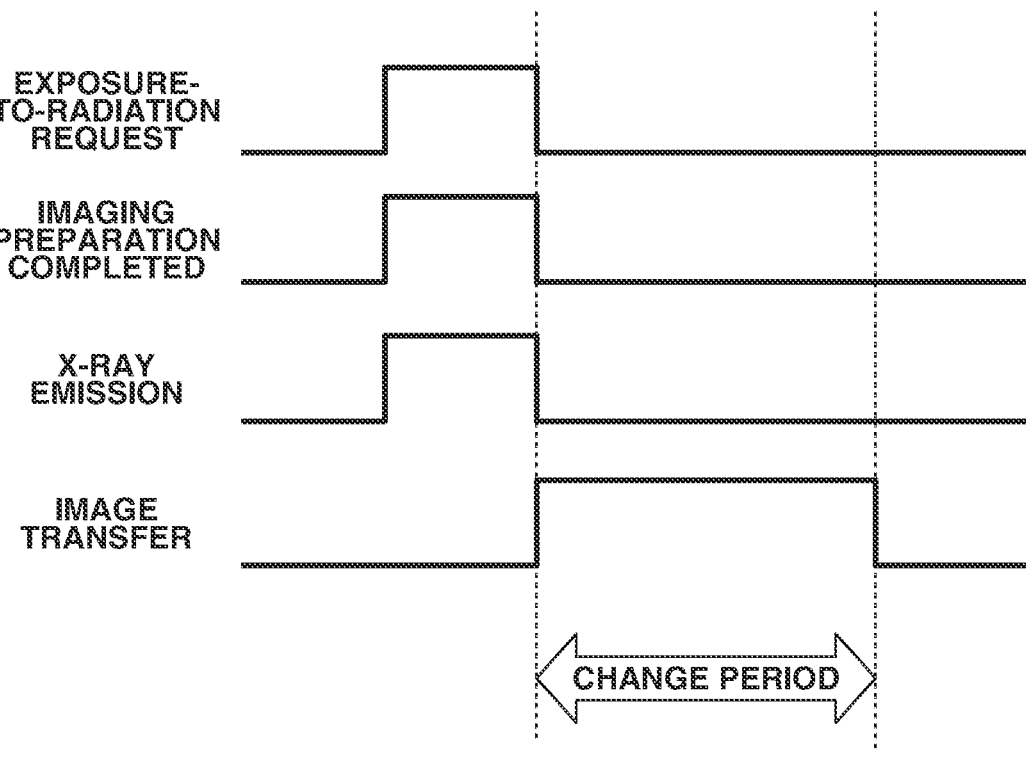
FIG. 5 illustrates a time period during which the control unit according to the first exemplary embodiment changes a communication configuration.

FIG. 5 illustrates an example of a time period during which the control unit 14 changes the communication configuration when the determination unit 18 of the radiographing apparatus 101 according to the present exemplary embodiment determines that the radiation image transmission is in progress. The operations performed since the radiation generation apparatus 106 issues an exposure-to-radiation request until the radiation is emitted is similar to that in FIG. 4.

The determination unit 18 determines whether the radiation image transmission via the first communication unit 2 is in progress. Further, if the determination unit 18 determines to perform the communication via the second communication unit 6, the control unit 14 limits the communication via the first communication unit 2 or the second communication unit 6. More specifically, when the radiation image transmission via the first wireless communication is being performed, the determination unit 18 as an example of a control unit performs control to disable at least one of the transmission and reception of information (information about the establishment of the first wireless communication) via the second wireless communication. If the determination unit 18 determines that the radiation image transmission is completed, the control unit 14 performs control to cancel the communication limitation.

Figure 6:
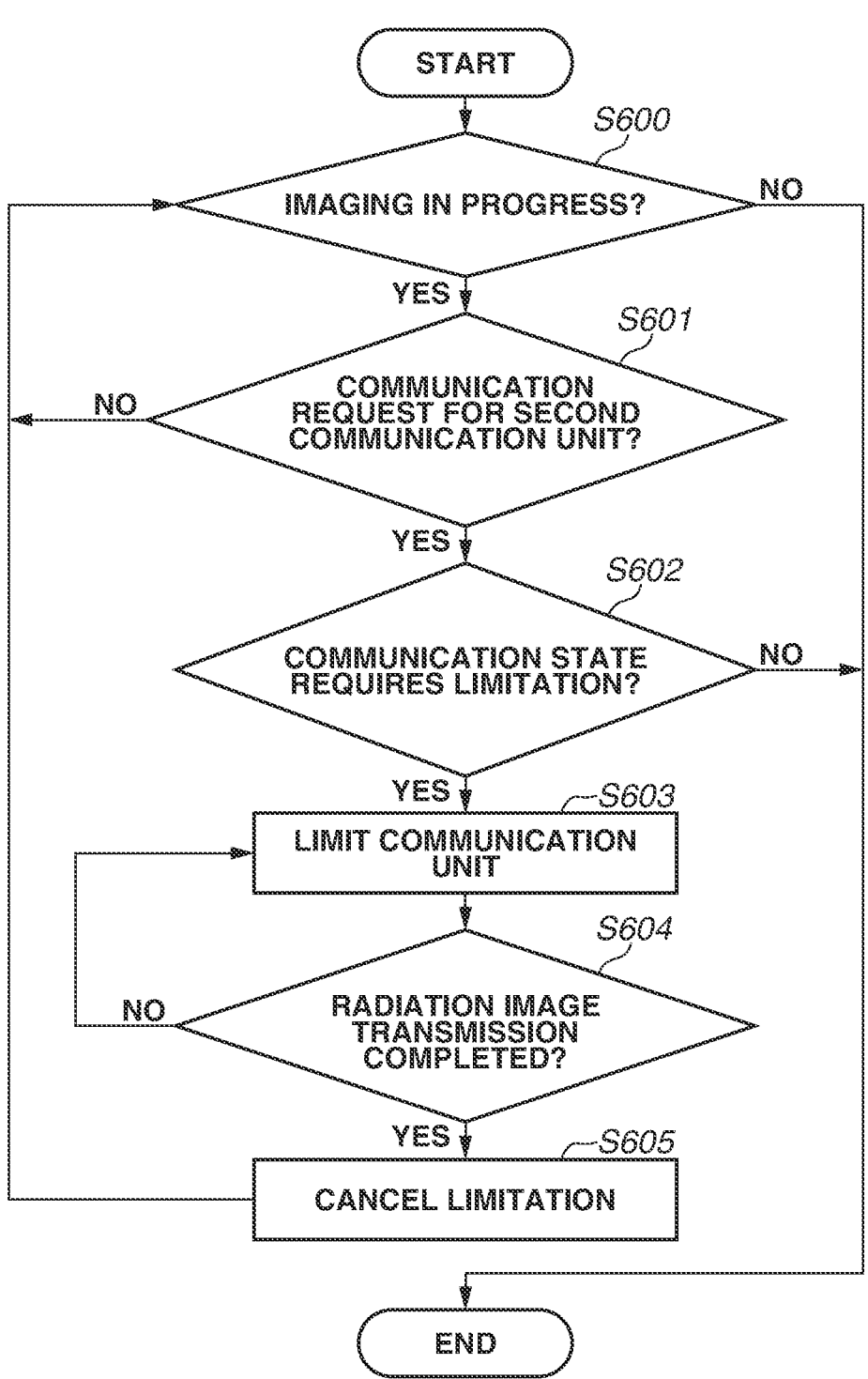
FIG. 6 is a flowchart illustrating operations of the radiographing apparatus according to the first exemplary embodiment.

FIG. 6 is a flowchart illustrating a method for controlling the radiographing apparatus 101 when the radiation image transmission is performed a plurality of times, such as in fluorography and image division transmission.

In step S600, the determination unit 18 determines whether the radiographing apparatus 101 is performing the radiographing specified by the information processing apparatus 102. If the radiographing apparatus 101 is performing the radiographing (YES in step S600), the processing proceeds to step S601. If the radiographing apparatus 101 is not performing the radiographing (NO in step S600), the processing ends the flowchart. For example, if the first communication unit 2 has transmitted the desired number of radiation images set from the information processing apparatus 102 to the radiographing apparatus 101, the radiographing is completed (not in progress).

As a method for transmitting a radiation image, the radiation detection unit 20 divides the generated one frame, and the first communication unit 2 transmits the division frame. The division of one frame is performed in such a way that the drive circuit 17 and the readout circuit 16 thin out pixels 200 disposed in the radiation detection unit 20, and the ADC 7 generates a digital signal to the control unit 14. The control unit 14 may thin out radiation images for one frame before performing communication via the first communication unit 2.

As another example of a method for determining whether the radiographing apparatus 101 is performing the radiographing, the determination unit 18 may determine whether an exposure-to-radiation request is issued from the radiation generation apparatus 106 or whether the display or status of the information processing apparatus 102 indicates that the radiographing is in progress.

In step S601, the determination unit 18 determines whether to perform the wireless communication based on the status of the transmission/reception communication buffer and/or the status of the communication controller. If the control unit 14 is preset to perform the communication via the second communication unit 6 upon operation on the operation unit 12, the determination unit 18 can also determine whether the operation on the operation unit 12 has been performed. If the determination unit 18 determines to perform the wireless communication via the second communication unit 6 (YES in step S601), the processing proceeds to step S602. If the determination unit 18 does not determine to perform the wireless communication via the second communication unit 6 (NO in step S601), the processing returns to step S600. The determination unit 18 performs the operation in step S600 again.

In step S602, the determination unit 18 determines the status of the radiation image communication via the first communication unit 2. If the first communication unit 2 is performing the radiation image transmission or is ready for the radiation image transmission (YES in step S602), the processing proceeds to step S603. If the first communication unit 2 is neither performing the radiation image transmission nor ready for the radiation image transmission (NO in step S602), the processing ends the flowchart, and the second communication unit 6 performs the wireless communication.

In step S603, the control unit 14 changes the communication configuration of the first communication unit 2 or the second communication unit 6 based on the result of the determination by the determination unit 18. The processing then proceeds to step S604.

In step S604, the determination unit 18 determines whether the first communication unit 2 completes the radiation image transmission or becomes not ready for the radiation image transmission. When the result of the determination is yes (YES in step S604), the processing proceeds to step S605. If the result of the determination is no (NO in step S604), the processing returns to step S603. In other words, the control unit 14 repeats the operations in steps S603 to S604 until the determination unit 18 determines that the state where the first communication unit 2 is performing the wireless communication or is ready for the wireless communication has ended.

In step S605, the control unit 14 cancels the communication configuration of the wireless communication via the first communication unit 2 or the second communication unit 6 that has been changed in step S603, and restores the communication configuration of the wireless communication before the change in step S603. The processing then returns to step S600. The determination unit 18 repeats steps S600 to 605 until the radiographing is completed. When the radiographing is completed (NO in step S600), the processing ends the flowchart.

Figure 7:
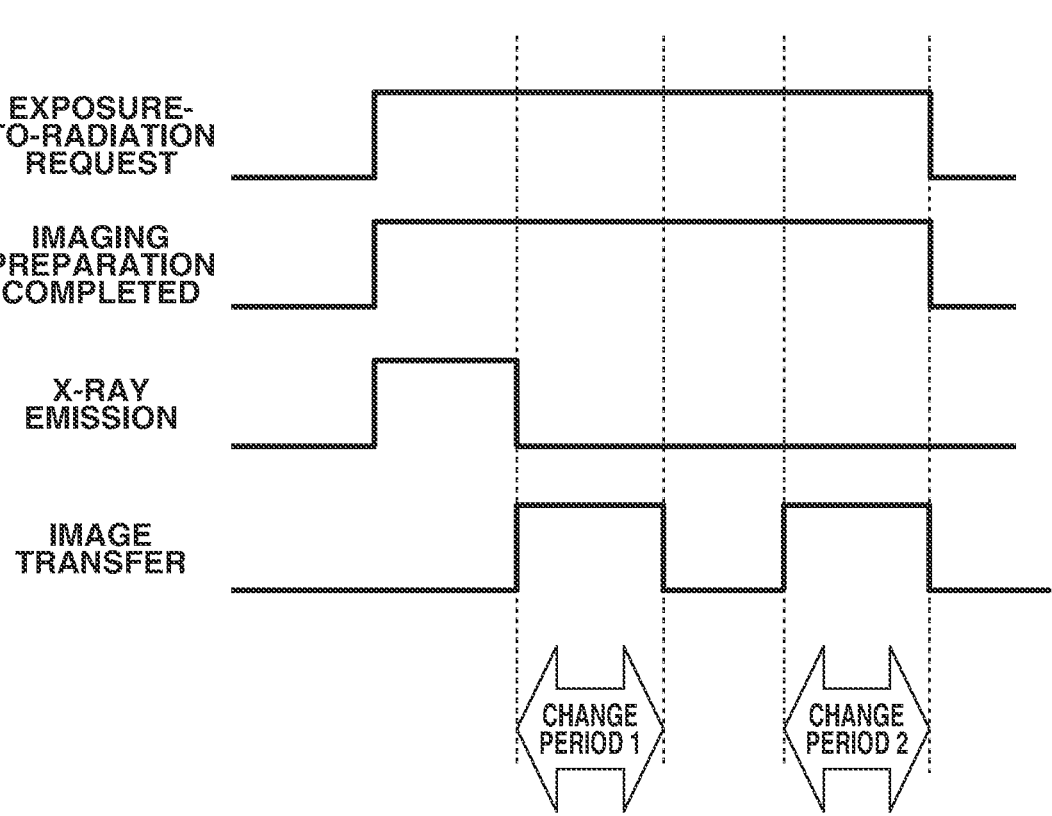
FIG. 7 illustrates a time period during which the control unit according to the first exemplary embodiment changes a communication configuration.

FIG. 7 is a time chart illustrating an example of a time period during which the control unit 14 changes the communication configuration in a case where the radiation image transmission is performed a plurality of times, for example, in fluorography and image division transmission. The operations since the radiation generation apparatus 106 issues an exposure-to-radiation request until the radiation emission is performed are similar to the operations in FIG. 4.

If the radiation generation apparatus 106 issues an exposure-to-radiation request to the radiographing apparatus 101, the determination unit 18 determines that the radiographing is in progress. The determination unit 18 also determines whether the radiation image transmission via the first communication unit 2 is in progress. If the determination unit 18 determines to perform the communication via the second communication unit 6, the control unit 14 changes the communication configuration of the first communication unit 2 or the second communication unit 6 (change period 1).

If the determination unit 18 determines that the radiation image transmission is completed, the control unit 14 performs control to cancel the change of the communication configuration. If the radiation generation apparatus 106 issues an exposure-to-radiation request to the radiographing apparatus 101, the determination unit 18 determines that the radiographing is in progress and then determines whether the radiation image transmission via the first communication unit 2 is in progress. Subsequently, the radiographing apparatus 101 performs similar processing to the change period 1 (change period 2).

Figure 8:
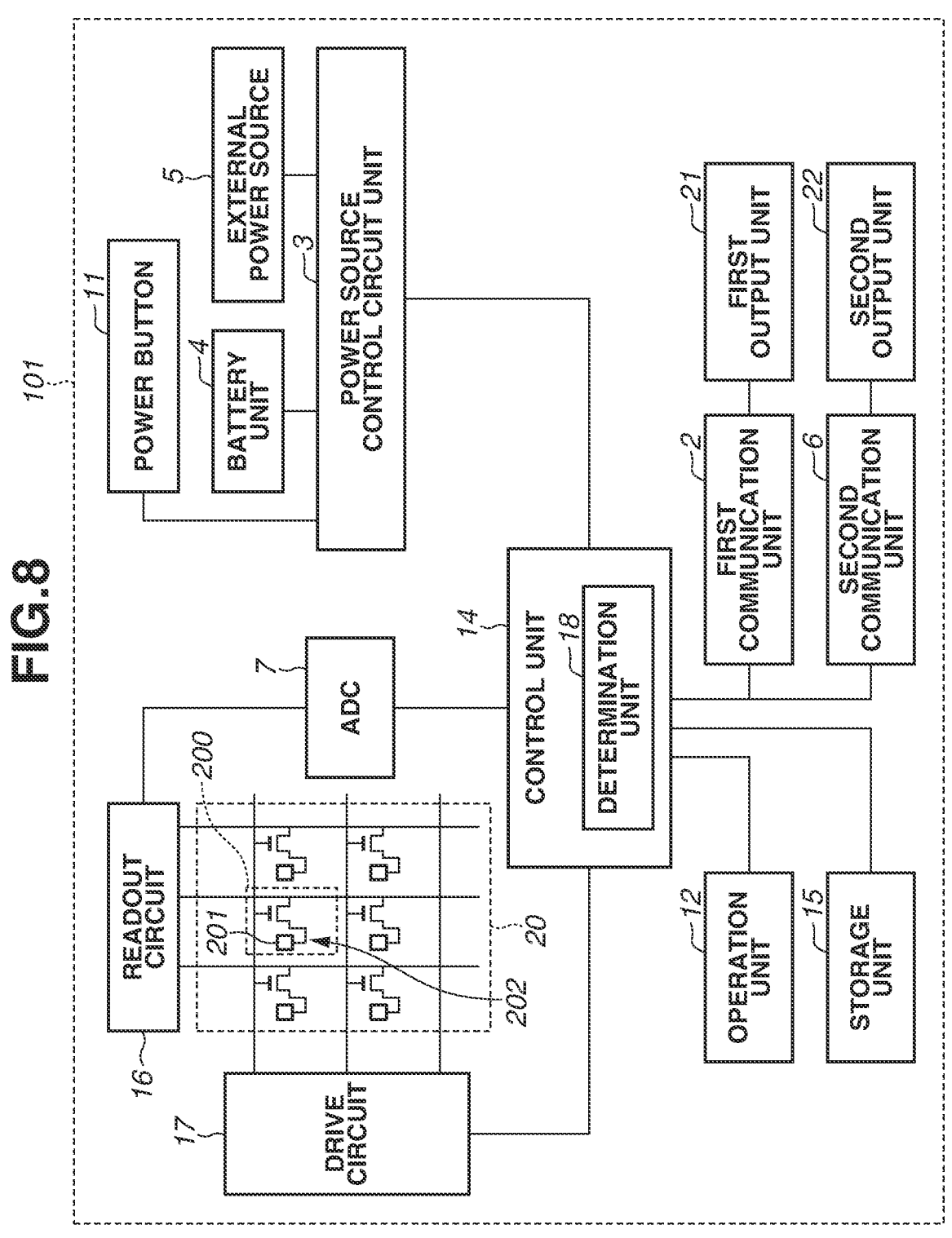
FIG. 8 is an example of an overall configuration of the essential part of the radiographing apparatus according to the first exemplary embodiment.

In the above descriptions, the first communication unit 2 and the second communication unit 6 are connected to the first output unit 21 as the same output unit via the output switching unit 19. However, the present exemplary embodiment is not limited thereto. As illustrated in FIG. 8, the first communication unit 2 and the second communication unit 6 may be provided with the first output unit 21 and the second output unit 22, respectively, as corresponding output units.

Figure 10:
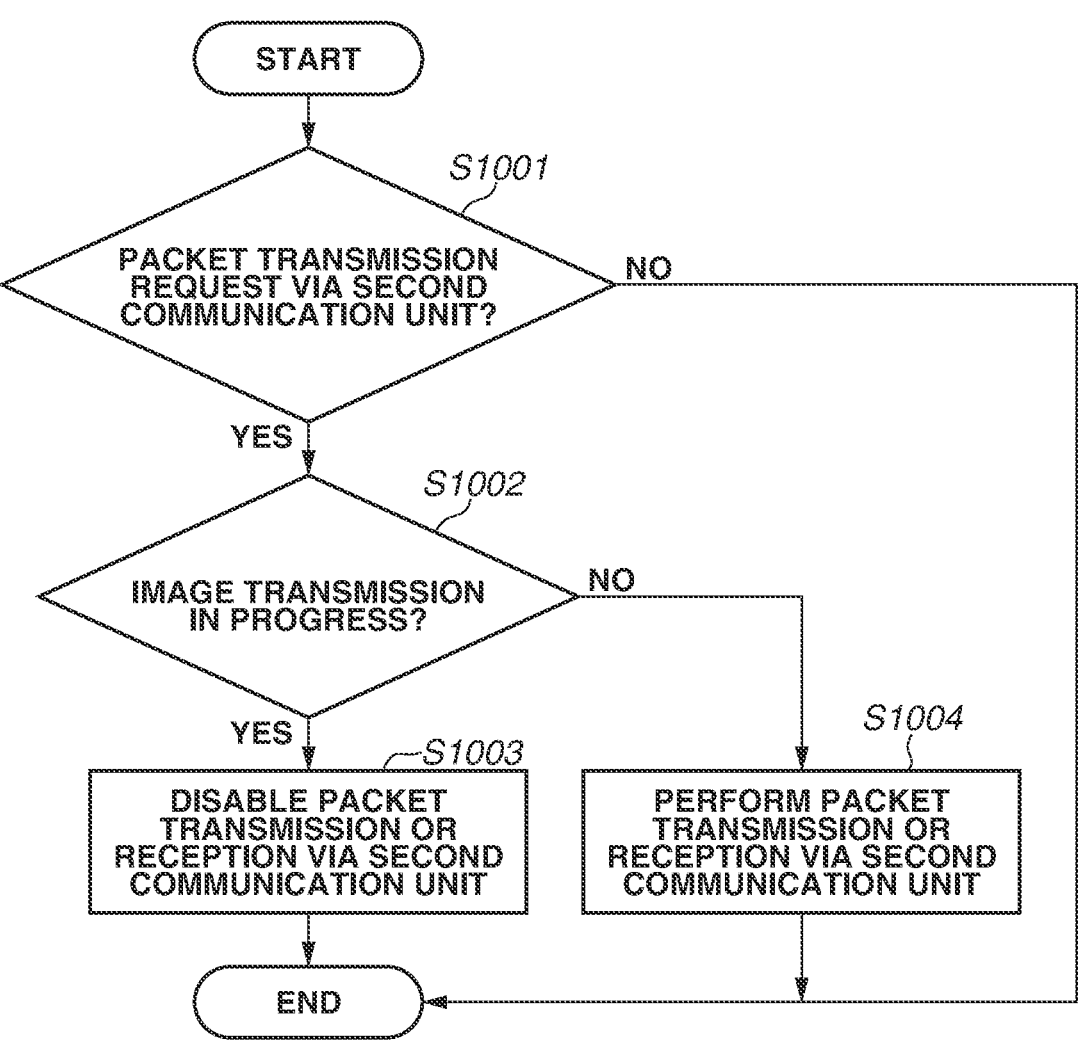
FIG. 10 is a flowchart illustrating operations of the radiographing apparatus according to the second exemplary embodiment.

FIG. 10 is a flowchart illustrating a method for controlling the radiographing apparatus 101 according to the present exemplary embodiment.

In step S1001, the determination unit 18 determines whether to perform the wireless communication via the second communication unit 6 based on the status of the transmission buffer and the status of the communication controller. If the control unit 14 is preset to perform the packet transmission via the second communication unit 6 upon operation on the operation unit 12, the determination unit 18 can also determine whether the operation on the operation unit 12 has been performed. If the determination unit 18 determines to perform the packet transmission via the second communication unit 6 (YES in step S1001), the processing proceeds to step S1002. For example, at the timing when an operation on the operation unit 12 is performed in step S1001, the control unit 14 may perform preparation operations (including module reset for the second communication unit 6 and packet header generation preparation) for transmitting the identifier of the radiographing system 100, and the SSID, encryption key, IP address, and other setting information required to establish the communication with the first communication unit 2.

When the determination unit 18 does not determine to perform the communication via the second communication unit 6, the control unit 14 does not perform the packet transmission, and the processing exits the flowchart.

In step S1002, the determination unit 18 determines whether the radiographing apparatus 101 is currently performing the radiation image transmission or is ready for the radiation image transmission to the information processing apparatus 102 via the first communication unit 2. The state where the radiographing apparatus 101 is ready for the radiation image transmission refers to a state where the radiographing apparatus 101 can perform the radiographing upon reception of an exposure-to-radiation request from the radiation generation apparatus 106 and then perform the radiation image transmission after the radiographing. When the result of the determination is yes (YES in step S1002), the processing proceeds to step S1003. If the result of the determination is no (NO in step S1002), the processing proceeds to step S1004.

In step S1003, the control unit 14 performs control to disable the packet transmission or reception via the second communication unit 6. If the packet transmission or reception is stopped, the control unit 14 may perform control not to start the packet transmission or reception via the second communication unit 6.

In step S1004, the control unit 14 controls the second communication unit 6 to perform the packet transmission or reception. For example, the second communication unit 6 transmit the identifier of the radiographing system 100, and the SSID, encryption key, IP address, and other setting information required to establish the communication with the first communication unit 2.

The above-described processing improves the communication speed and communication quality for the radiation image transmission when the radiographing apparatus 101 performs the radiation image transmission via the first communication unit 2.

Figure 9:
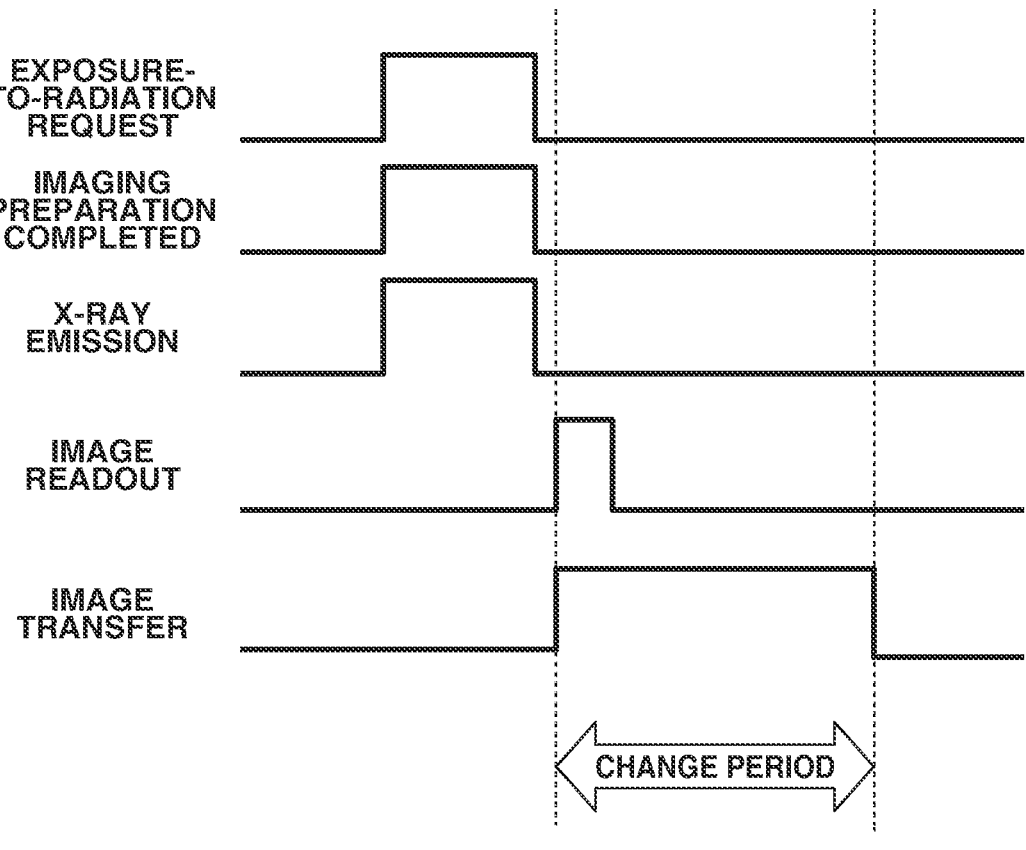
FIG. 9 illustrates a time period during which a control unit according to a second exemplary embodiment changes a communication configuration.

FIG. 9 illustrates an example of a time period during which the control unit 14 changes the communication configuration to a state where the radiographing apparatus 101 is attempting to perform the radiation image transmission according to a second exemplary embodiment. FIG. 10 illustrates an example of an operation when the determination unit 18 determines an operation for reading out image signals (electric charges) as a state where the radiographing apparatus 101 is attempting to perform the radiation image transmission. The operations performed since the radiation generation apparatus 106 issues an exposure-to-radiation request until an X-ray is emitted is similar to that in FIG. 4.

If communication is performed around the radiographing apparatus 101 in reading out image signals, the communication may affect the generation of image signals (electric charges) possibly causing noise in an image. The present exemplary embodiment therefore stops the wireless communication via the second communication unit 6 during this period.

The determination unit 18 determines whether to apply a drive signal to the radiation detection unit 20 via the drive circuit 17 to start an operation for reading out image signals (electric charges). Then, when the determination unit determines that the radiation image transmission via the first communication unit 2 is in progress, the control unit 14 stops the wireless communication via the second communication unit 6.

If the determination unit 18 determines that the radiation image transmission is completed, the control unit 14 performs control to cancel the changed communication configuration to restore the communication configuration before the change. The above-described unit stops communication during a read operation, making it possible to restrain the influence on image noise during an image signal read operation. A state where the radiographing apparatus 101 is attempting to perform the radiation image transmission may include a state where a drive signal is applied to the radiation detection unit 20 via the drive circuit 17 to accumulate an image signal, and a dummy read operation as a read operation in a state where the radiation emission is not performed.

A short-distance wireless communication unit used for linking to an access point and a wireless communication unit used for the radiation image transmission and reception may use a duplicated frequency band (channel) for wireless communication. Conventional radiographing systems do not take radio wave interferences in such a case into consideration. Thus, if a radio wave interference occurs, the communication speed and communication quality may possibly be degraded. The disclosure of an exemplary embodiment of the present disclosure is directed to improving the communication speed and communication quality. The radiographing apparatus according to the exemplary embodiment of the present disclosure includes a first communication unit for transmitting a radiation image captured in radiographing, via the first wireless communication with an access point. The radiographing apparatus according to the exemplary embodiment of the present disclosure further includes a second communication unit for transmitting and receiving the information about the establishment of the first wireless communication, via second wireless communication with a communication device. The radiographing apparatus according to the exemplary embodiment of the present disclosure further includes a control unit for controlling the first communication and the second wireless communication. When the radiation image transmission via the first wireless communication is being performed (or imaging preparation operations for the radiographing have been completed), the control unit according to the exemplary embodiment of the present disclosure performs control to disable at least one of the transmission and reception of the information about the establishment of the first wireless communication, via the second wireless communication. The exemplary embodiment thereby makes it possible, for example, to improve the communication speed and communication quality.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2023-045119, filed Mar. 22, 2023, which is hereby incorporated by reference herein in its entirety.

What is claimed is:

1. A radiographing apparatus for performing radiographing, comprising:

a first communication unit configured to transmit a radiation image captured in the radiographing, via first wireless communication with an access point;

a second communication unit configured to transmit information and receive the information about an establishment of the first wireless communication, via second wireless communication with a communication device; and a control unit configured to control the first wireless communication and the second wireless communication, wherein, in a case where the radiation image transmission is being performed via the first wireless communication, the control unit performs control to disable at least one of transmission of the information and reception of the information via the second wireless communication.

2. The radiographing apparatus according to claim 1, wherein, in a case where an operation unit for the second wireless communication is pressed and the radiation image transmission is not being performed via the first wireless communication, the control unit performs a packet transmission via the second wireless communication, and wherein, in a case where the operation unit is pressed and the radiation image transmission is being performed via the first wireless communication, the control unit performs control to disable the packet transmission via the second wireless communication.

3. The radiographing apparatus according to claim 1, wherein, in a case where imaging preparation operations for the radiographing have been completed, the control unit performs control to disable at least one of transmission of the information and reception of the information via the second wireless communication.

4. A radiographing apparatus for performing radiographing, comprising:
a first communication unit configured to transmit a radiation image captured in the radiographing, via first wireless communication with an access point;
a second communication unit configured to transmit information and receive the information about an establishment of the first wireless communication, via second wireless communication with a communication device; and
a control unit configured to control the first wireless communication and the second wireless communication,
wherein, in a case where imaging preparation operations for the radiographing have been completed, the control unit performs control to disable at least one of transmission of the information and reception of the information via the second wireless communication.

5. The radiographing apparatus according to claim 3,
wherein, in a case where an operation unit for the second wireless communication is pressed and imaging preparation operations for the radiographing are not completed, the control unit performs control to perform a packet transmission via the second wireless communication, and
wherein, in a case where the operation unit is pressed and the imaging preparation operations for the radiographing have been completed, the control unit performs control to disable the packet transmission via the second wireless communication.

6. The radiographing apparatus according to claim 1, wherein the control unit performs control not to stop or start the second wireless communication to perform control to disable at least one of transmission of the information and reception of the information via the second wireless communication.

7. The radiographing apparatus according to claim 1, wherein, upon detection of the end of the radiation image transmission via the first wireless communication, the control unit performs control to cancel a changed communication configuration in the first wireless communication or the second wireless communication to restore the communication configuration before a change.

8. The radiographing apparatus according to claim 1, wherein the first communication unit is a local area network (LAN).

9. The radiographing apparatus according to claim 1, wherein the second communication unit is a personal area network (PAN).

10. A radiographing system comprising:
the radiographing apparatus according to claim 1;
the access point; and
the communication device.

11. A radiographing system comprising:
the radiographing apparatus according to claim 4;
the access point; and
the communication device.

12. A radiographing method for performing radiographing, the method comprising:
transmitting a radiation image captured in the radiographing, via first wireless communication with an access point;
transmitting information and receiving the information about an establishment of the first wireless communication, via second wireless communication with a communication device; and
performing, in a case where the radiation image transmission is being performed via the first wireless communication, control to disable at least one of the transmission of the information and reception of the information via the second wireless communication.

13. A radiographing method for performing radiographing, the method comprising:
transmitting a radiation image captured in the radiographing, via first wireless communication with an access point;
transmitting information and receiving the information about an establishment of the first wireless communication, via second wireless communication with a communication device; and
performing, in a case where imaging preparation operations for the radiographing have been completed, control to disable at least one of the transmission of the information and reception of the information via the second wireless communication.

14. A non-transitory computer-readable storage medium storing a program for causing a computer to execute the method according to claim 12.

15. A non-transitory computer-readable storage medium storing a program for causing a computer to execute the method according to claim 13.

* * * * *